United States Patent [19]
LeFree et al.

[11] Patent Number: 5,908,387
[45] Date of Patent: Jun. 1, 1999

[54] DEVICE AND METHOD FOR IMPROVED QUANTITATIVE CORONARY ARTERY ANALYSIS

[75] Inventors: Michelle Tamara LeFree; Joseph Sitomer, both of Ann Arbor, Mich.

[73] Assignee: Quinton Instrument Company, Bothell, Wash.

[21] Appl. No.: 08/878,267

[22] Filed: Jun. 18, 1997

Related U.S. Application Data

[60] Provisional application No. 60/021,232, Jun. 21, 1996.
[51] Int. Cl.$^6$ .................................................. A61B 5/00
[52] U.S. Cl. .......................................... 600/425; 600/433
[58] Field of Search ................................... 600/407, 414, 600/415, 417, 425, 427, 431, 433

[56] References Cited

U.S. PATENT DOCUMENTS

| | | | |
|---|---|---|---|
| 1,563,362 | 12/1925 | Herradora | 378/164 |
| 1,953,249 | 4/1934 | Michel | 250/34 |
| 3,010,223 | 11/1961 | Alderson | 35/17 |
| 3,111,582 | 11/1963 | Levi | 250/59 |
| 3,881,110 | 4/1975 | Hounsfield et al. | 250/360 |
| 4,126,789 | 11/1978 | Vogel et al. | 250/505 |
| 4,187,423 | 2/1980 | Ehrhardt | 250/312 |
| 4,279,252 | 7/1981 | Martin | 128/349 R |
| 4,296,329 | 10/1981 | Mirabella | 250/491 |
| 4,331,869 | 5/1982 | Rollo | 250/252 |
| 4,333,010 | 6/1982 | Miller | 250/252 |
| 4,344,183 | 8/1982 | Jacobson | 378/207 |
| 4,352,020 | 9/1982 | Horiba et al. | 378/18 |
| 4,436,684 | 3/1984 | White | 264/138 |
| 4,460,832 | 7/1984 | Bigham | 250/505.1 |
| 4,472,829 | 9/1984 | Riederer et al. | 378/207 |
| 4,646,334 | 2/1987 | Zerhouni | 378/18 |
| 4,649,561 | 3/1987 | Arnold | 378/207 |
| 4,655,716 | 4/1987 | Hoevel | 434/267 |
| 4,663,772 | 5/1987 | Mattson et al. | 378/18 |
| 4,724,110 | 2/1988 | Arnold | 264/102 |
| 4,771,469 | 9/1988 | Wittenburg | 382/25 |
| 4,782,502 | 11/1988 | Schulz | 378/18 |
| 4,794,631 | 12/1988 | Ridge | 378/207 |
| 4,827,492 | 5/1989 | Klauzs | 378/99 |
| 4,860,331 | 8/1989 | Williams et al. | 378/163 |
| 4,873,707 | 10/1989 | Robertson | 600/425 |
| 4,922,915 | 5/1990 | Arnold et al. | 128/653 R |
| 5,005,578 | 4/1991 | Greer et al. | 600/414 |
| 5,052,035 | 9/1991 | Krupnick | 378/163 |
| 5,178,146 | 1/1993 | Giese | 600/415 |
| 5,236,363 | 8/1993 | Sandrik et al. | 434/267 |
| 5,239,569 | 8/1993 | Saleh et al. | 378/163 |
| 5,245,184 | 9/1993 | Skretting et al. | 250/252.1 |
| 5,323,111 | 6/1994 | Suzuki | 324/309 |
| 5,335,260 | 8/1994 | Arnold | 378/207 |
| 5,383,234 | 1/1995 | Russell | 378/164 |
| 5,416,816 | 5/1995 | Wenstrup et al. | 378/18 |
| 5,421,330 | 6/1995 | Thirion et al. | 128/653.1 |
| 5,458,111 | 10/1995 | Coin | 128/747 |
| 5,602,891 | 2/1997 | Pearlman | 378/62 |
| 5,699,799 | 12/1997 | Xu et al. | 128/653.1 |

*Primary Examiner*—Ruth S. Smith
*Attorney, Agent, or Firm*—Graybeal Jackson Haley LLP

[57] ABSTRACT

The present invention is generally directed to one or more devices and a method for improving quantitative coronary artery analysis. The devices which may be used with the present invention include an improved angiographic image quality phantom, an improved arterial phantom and the initial imaging of the procedure catheter. One or all of these devices may be used to increase the accuracy and quality of the arterial measurements provided by an edge detection analysis program. The method includes the initial imaging of the image quality phantom to allow for the correction of various geometric distortions present in an imaging system. Next, the tip of the procedure catheter and the arterial phantom are imaged to create an improved regression curve for the imaging system an to allow for increased accuracy in the use of the procedure catheter as a basis for the determination of the calculated artery diameters.

6 Claims, 5 Drawing Sheets

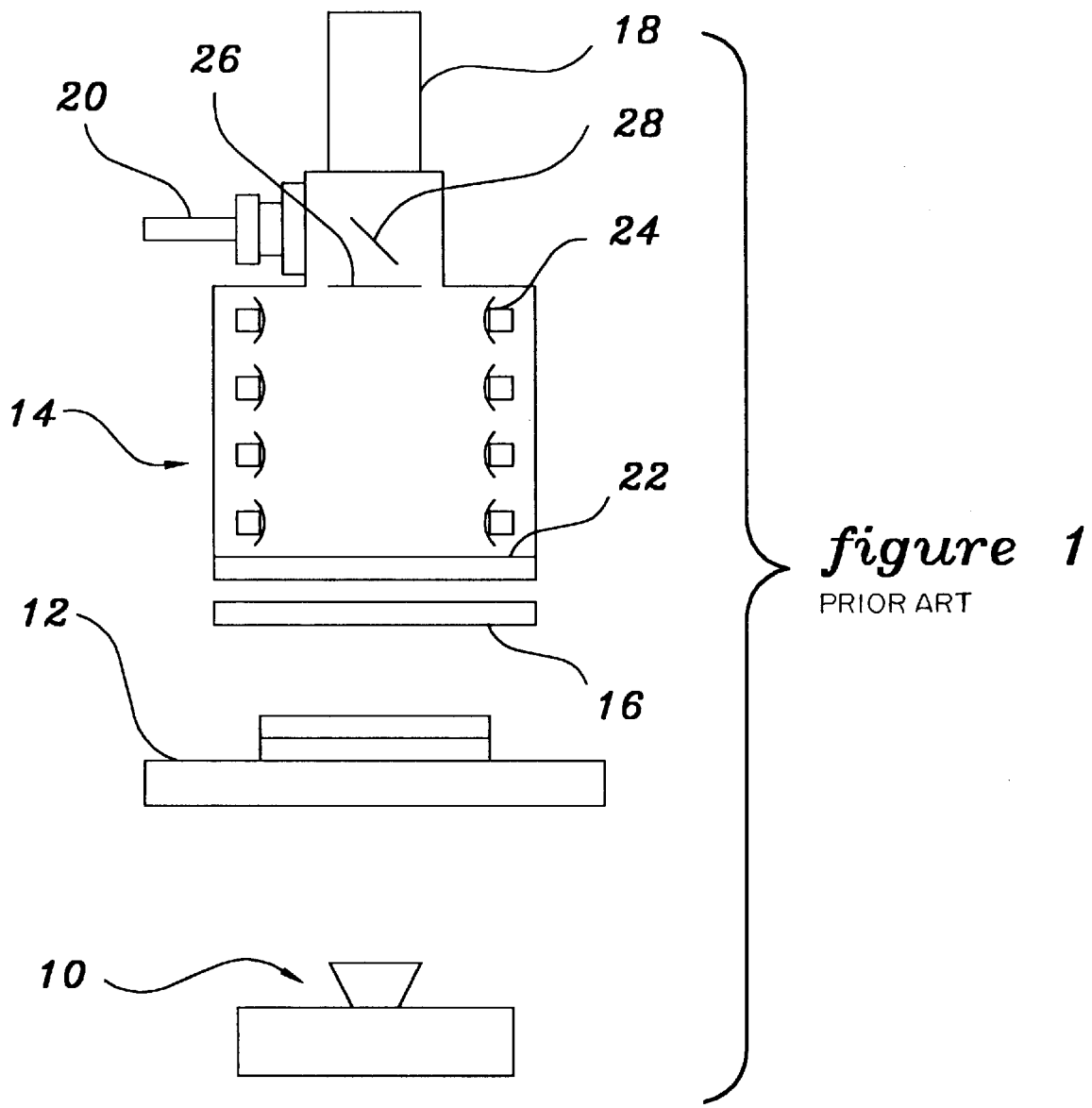
figure 1
PRIOR ART

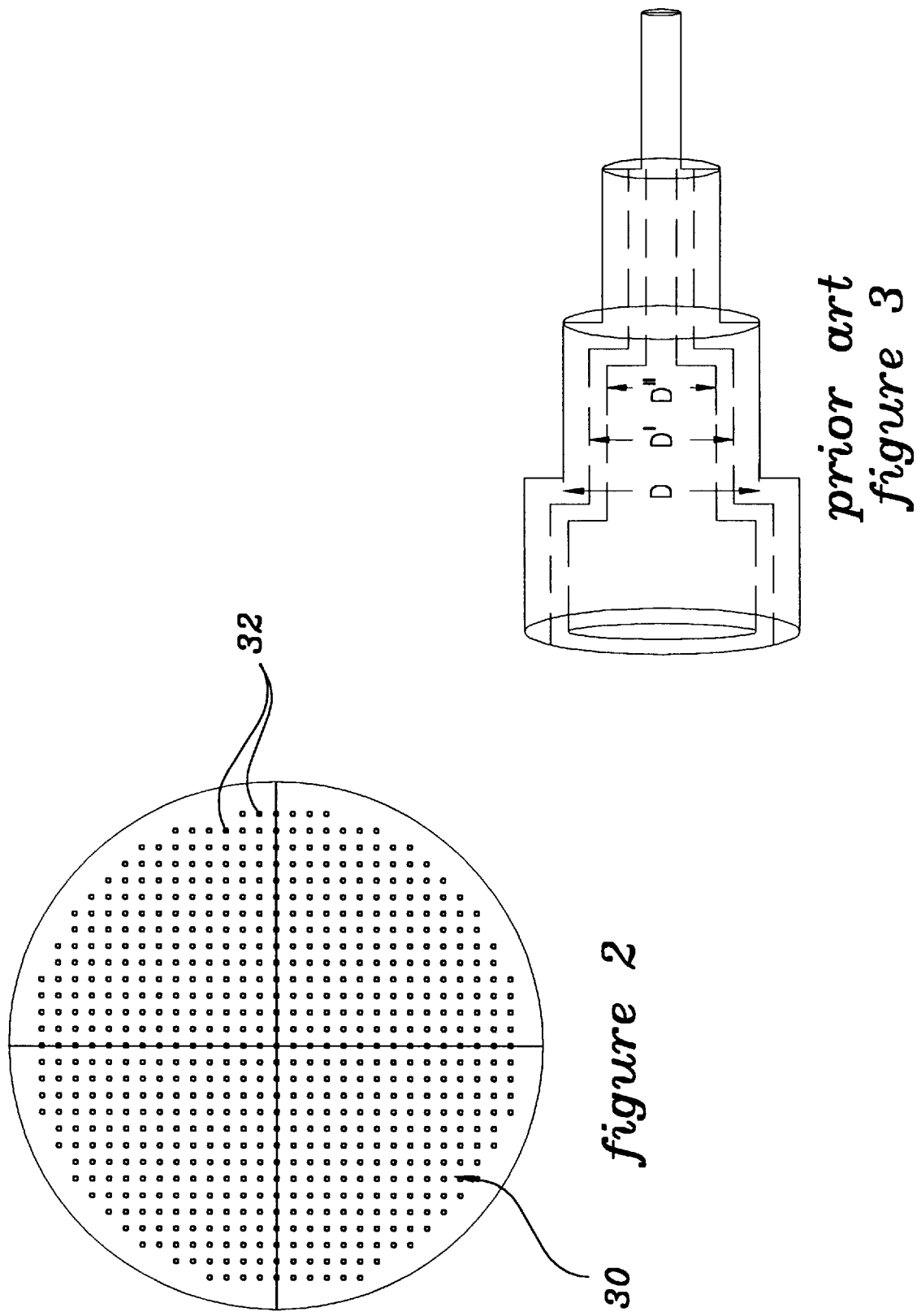
figure 2
prior art
figure 3

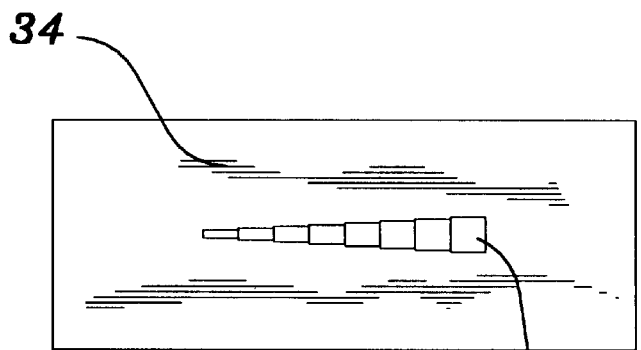
figure 4
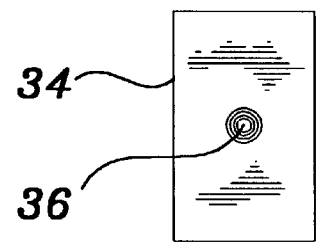
figure 6
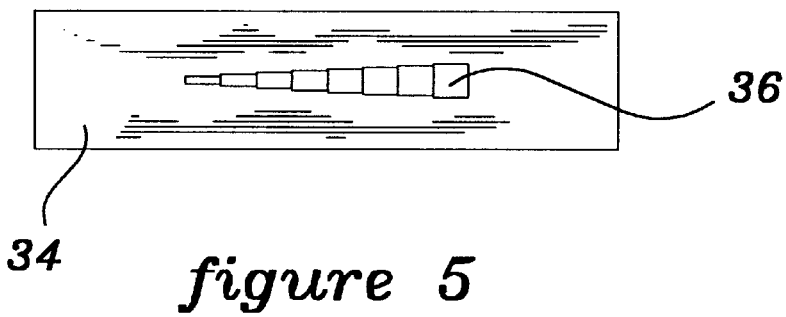
figure 5
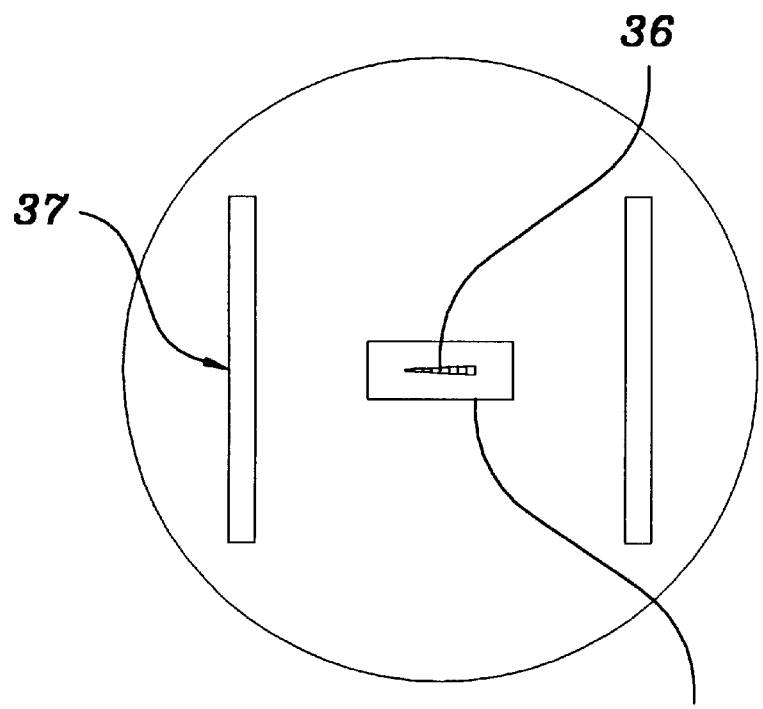
figure 7

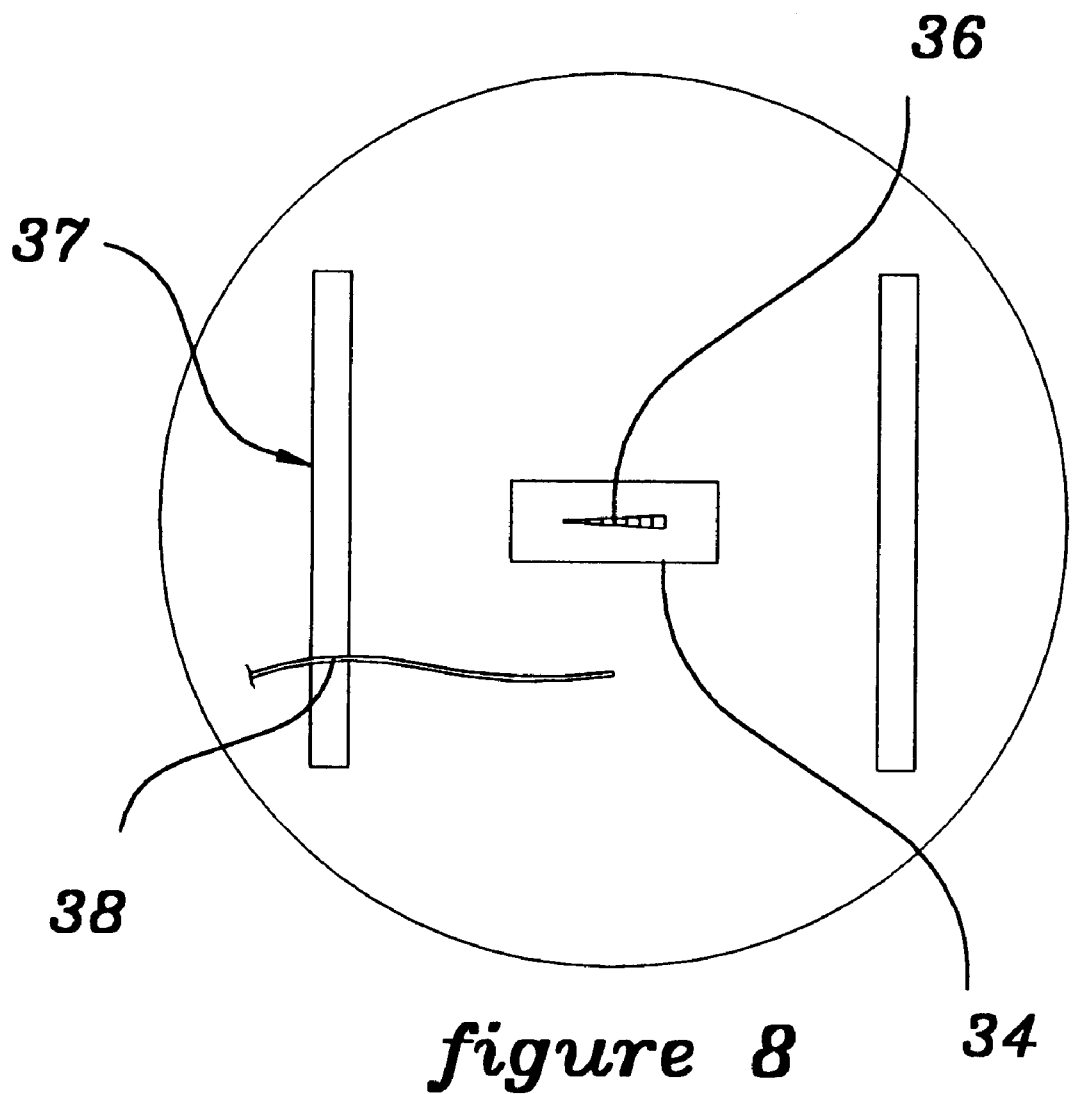
figure 8

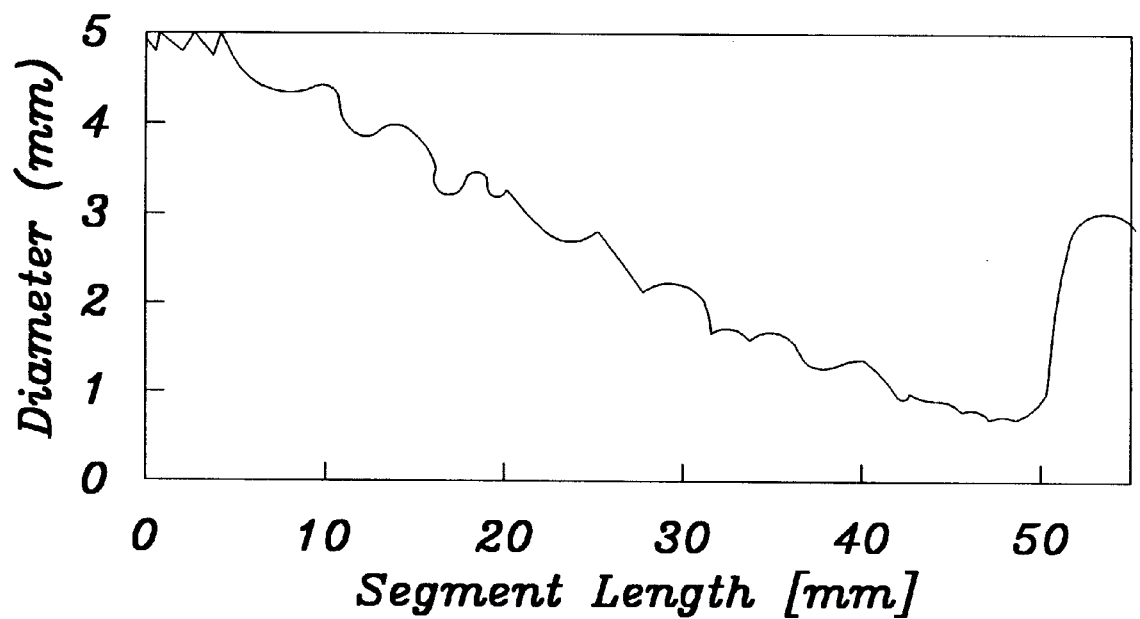
figure 9A
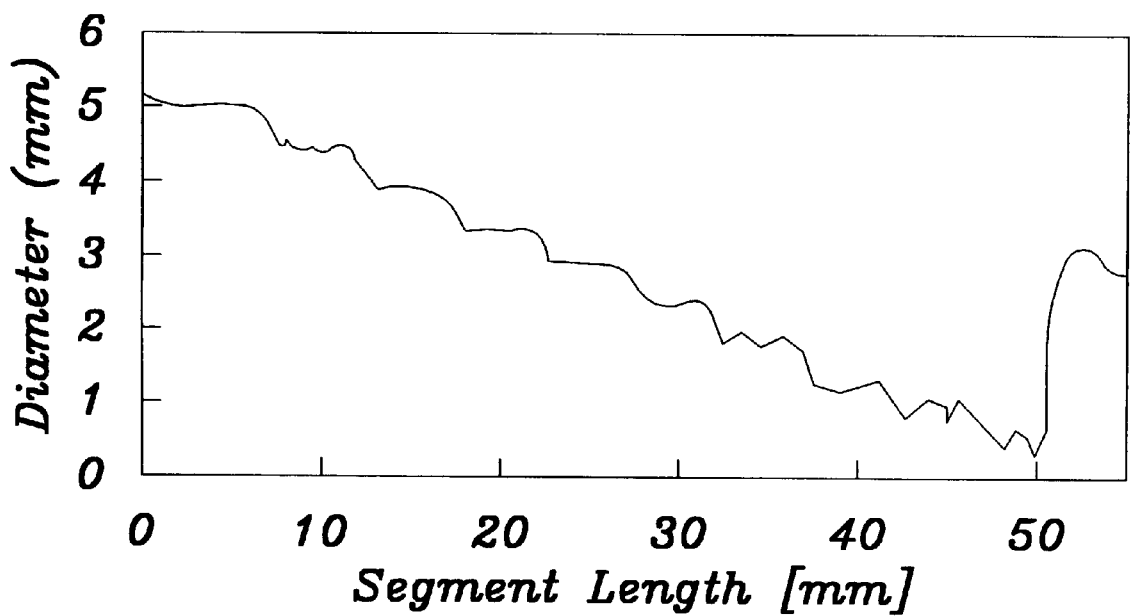
figure 9B

1

DEVICE AND METHOD FOR IMPROVED QUANTITATIVE CORONARY ARTERY ANALYSIS

The present application is based on Provisional application U.S. Serial No. 60/021,232 filed on Jun. 21, 1996.

FIELD OF THE INVENTION

The present invention relates generally to system for improving the calibration of a cardiac analysis program and more particularly to an improved system for performing coronary artery analysis and more particularly to an improved system using a novel arterial phantom having known internal diameters in combination with an angiographic catheter and an improved image quality phantom to increase the accuracy of existing quantitative coronary artery analysis programs.

BACKGROUND OF THE INVENTION

During angiographic or other diagnostic procedures which use X-Rays, a system similar to that shown generally in FIG. 1 is used. The system generally includes an X-Ray tube 10 which emits X-Rays from a general point source. The X-Ray tube is positioned under a table 12 on which the patient or other object of interest is positioned. In order to provide for X-Ray photography, cinegraphic recording and/or viewing of the subject, and image intensifier 14 is positioned above the subject.

The bottom surface of the image intensifier 14 includes a grid 16 having a plurality of narrowly spaced strips thereon in order to attenuate scattered X-Rays so that only the X-Rays which pass through the subject directly from the X-Ray tube are recorded by the recording medium 20. The top of the image intensifier includes a TV or similar camera 18 to allow the physician to dynamically view the subject of the study. For example, the heart or other organ of a patient may be viewed through the camera to allow the physician the ensure the proper positioning and observe the operation heart or other organ. Additionally, the top portion of the image intensifier 14 also typically includes a recording medium 20 such as a film camera or digital recording medium to record the study for later review and analysis. The image intensifier incorporates a phosphorous screen 22 and a series of focusing coils 24 which tend to cause the X-Ray beams to be directed toward a phosphorous output lens 26. The beam from the output lens is split by a beam splitter 28 to provide output to the TV camera 18 and recording medium 20.

Current systems which are used to analyze coronary arteries during diagnostic angiographic procedures include automatic analysis programs to calculate the dimensions of the arteries of a patient. While these programs have been used for many years, the programs suffer from certain inaccuracies which result from distortions that occur during the image acquisition process as well as limitations in the sharpness of the pixels of the acquired image. For example, various studies have shown that the accuracy of the analysis programs decreases as the size of the artery of interest decreases and it is the arteries having the reduced sizes that are of particular interest to the cardiologist.

One of the major sources of image distortion with the current systems is geometric distortion. Geometric distortion results in pincushion or barrel distortion of the image and may result from the lenses and focusing coils in the imaging system as well as passage of the X-Rays from the conical or point source of the X-Ray tube to the generally planar grid 16 and image intensifier 14. This type of distortion may result in an image which is concave (pincushion) or convex (barrel) shaped near the edges of the image. Attempts to overcome this type of distortion include calibration of the imaging system when it is installed using a platform phantom having a plurality of lead lines. The lead lines are aligned in a grid shape horizontally and vertically along the platform with a known distance of 1 cm between each other. Although this procedure provides the program with the ability to correct for the calibrated geometric distortion of the system, geometric distortion also arises as the components of the system age or are replaced. Additionally, because there is a strong desire to minimize the dose of X-Rays that the patients are exposed to, the images include noise distortion and the images of the lead lines lose their sharpness around their edges. Additionally, the use of the lead lines does not present an accurate depiction of the absorption of the X-Rays for the organs of interest in a patient because the lead lines distort the X-Rays of the image system in different proportions than the organs of interest of the patient. As a result of the foregoing, the calibration analysis may include a certain amount of error which is then passed on to the calibrated images of the analysis program. Despite these difficulties, it is still desirable to provide an initial or partial correction for geometric distortion.

A further approach to improving image quality and analysis of the artery sizes involves the calibration of the analysis program using the procedure catheter. In the current approach, the outer diameter of the procedure catheter is assigned as a known distance and the areas of interest are then comparatively analyzed based on this distance. Difficulties in this approach arise from the lack of image sharpness inherent in the X-Ray type of imaging system as well as from the many different manufacturers and varieties of catheters which are available today. Further complicating the attempts to calibrate the analysis programs based on the catheter diameter is the fact that the catheters are made of various materials, each of which absorb and scatter the X-Rays differently. Each of these difficulties is then exacerbated by the magnification of the image for use in the analysis program. Despite this, the use of a procedure catheter to calibrate the analysis program is beneficial because the procedure catheter is useful as a reference to compare to the arteries because the absorption characteristics of the X-Rays for the catheters and arteries have greater similarities between each other than the lead lines and arteries. Additionally, the similarity in object size, dimension and object contrast between the procedure catheter and the nearby artery provides a useful reference for identifying the walls of the arteries.

Based on the foregoing, there remains a need for improved calibration or error correction devices and a method of their use to improve the quality of existing analysis programs for imaging systems.

Furthermore, there remains a need for a reliable and consistent calibration or error correction system which may be used to compare the relative differences between imaging systems to allow the images to be analyzed by a common analysis system without introducing additional errors.

SUMMARY OF THE INVENTION

An advantage of the present invention is that it provides a readily reproducible image system specific correction which allows for the accurate comparison of the procedure catheter and arterial cross-sections.

Another advantage of the present invention is that it provides a reliable method to compensate for deviations in the analysis program from the ideal regression curve caused by image system distortion.

Yet another advantage of the resent invention is that it permits calculated arterial diameters to relate directly to known procedure catheter diameters.

Yet another advantage of the system of the present invention is that it reduces the procedure induced errors which occur during the initial calibration of the image system and also increases the accuracy of the comparative calculations between the procedure catheter and the artery.

The present invention includes improvements in the imaging phantom, as well as improvements in the calculation of the imaged catheter size and dimensions. The imaging phantom of the present invention preferably includes a grid pattern which is made of bronze balls having a diameter of about 1 mm. The use of bronze balls rather than the traditional lead lines is preferred because the absorption characteristics of bronze more closely resembles the absorption characteristics of the iodine based dyes which are used during the imaging procedure. Additionally, the smaller size is chosen to more closely approximate the size of the arteries of interest.

The improvements in the calculation of the size of the imaged procedure catheter and artery include the use of an image quality phantom having a dye filled telescopic-shaped interior that is compared directly to the imaged procedure catheter so that the imaged dimension of the procedure catheter may be compared directly to a variety of known dimensions present in the imaged quality phantom. The body of the image quality phantom is formed of a material which approximates the absorption characteristics of the arteries of the patient. The results of this comparison may then be used to identify the absorption characteristics of the procedure catheter and to correct the distortion and image degradation present in the image provided to the analysis program at each of the known dimensions of the image quality phantom through the use of a regression curve which is applied during the final edge detection pass of the analysis program to modify edge placement by the analysis program. Initial studies indicate that this comparison significantly increases the accuracy of the analysis program, particularly for the smaller diameter measurements of the artery.

As described more fully herein, the present invention provides a system for overcoming many of the inherent limitations of the current level of reliance on the procedure catheter as a scaling device to compensate for geometric magnification in current analysis programs. Among the benefits of the present invention are the abilities to measure, on an imaging system specific basis, the overall regression curve for diameter response of the analysis program and the ability to relate the calipered diameter of a particular procedure catheter to the overall regression curve of the analysis program. Additionally, the present invention allows the user to compensate for deviations from the ideal linear response for the specific imaging system.

The method of the present invention generally includes a radiographic phantom consisting of a series of cylindrical model arterial segments spanning the range of diameters encountered in coronary angiography (0.5 mm to 5.0 mm). The segments of the phantom are filled with an iodinated material of the concentration of standard iodine contrast medium, are arranged coaxially, end-to-end, in 5 mm lengths and imbedded in a block of tissue equivalent absorber. This phantom is imaged in-vitro along side a tip of the particular procedure catheter which is to be used clinically. The analysis program is applied to the image of the phantom and the procedure catheter tip at a sampling density several times that employed clinically to ensure precise sampling at each diameter. This method yields an imaging system specific diameter regression curve over the range of diameters represented and a ratio of the calipered to detected procedure catheter diameters. The ratio is applied as a scaler correction to the regression curve to compensate for any difference between detected and calipered procedure catheter diameters. The resulting scaler-corrected regression data is used to derive diameter-specific correction factors to linearize the diameter response of the analysis program for a particular imaging system and procedure catheter. Tables of these corrected regression curves are stored and used in subsequent clinical applications of the analysis program. The result is improved linearity of diameter response as well as increased precision of analysis program results under varying imaging conditions using different imaging systems.

BRIEF DESCRIPTION OF THE INVENTION

FIG. 1 is a schematic drawing of a typical imaging system;

FIG. 2 is a top view of the image quality phantom of the present invention;

FIG. 3 is a top view of a prior art phantom as disclosed in U.S. Pat. No. 4,873,707;

FIG. 4 is a top view of the arterial phantom of the present invention;

FIG. 5 is a side view of the arterial phantom of the present invention;

FIG. 6 is an end view of the arterial phantom of the present invention;

FIG. 7 is a top view of the arterial phantom of the present invention placed on the table 12 of the imaging system;

FIG. 8 is a top view of the arterial phantom of the present invention and a portion of the procedure catheter placed on the table 12 of the imaging system;

FIGS. 9A and 9B are comparative plots with and without the calibration method of the present invention, respectively.

DETAILED DESCRIPTION OF THE PRESENT INVENTION

Although each of the individual devices are described herein as being part of the overall system to improve the accuracy of the analysis program, it is not believed to be necessary that each of the devices and each step in the method described below be present to provide significant improvement in existing analysis programs.

As shown in FIG. 2, the image quality phantom 30 of the present invention includes a series of spaced apart ball shaped members 32. These ball shaped members 32 are preferably made of bronze to closely approximate the absorption characteristics of the imaging material. In angiographic procedures, the imaging material is typically an iodine based material such as the imaging material sold as RENOGRAPHIN. The diameter of the ball shaped members 32 is preferably about 1 mm so that the each imaged ball shaped member has a diameter which is similar to the diameter of the arteries of interest. Additionally, the centers of each ball shaped member 32 are spaced apart from each other a constant distance such as 1 cm. The overall diameter of the image quality phantom 30 is sufficient to cover the entire image field of the image system when the image quality phantom 30 is placed on the table 12 of the image system. In the preferred form of the present embodiment, the diameter is about 33.5 cm and has a thickness of about one-eighth inch to provide the desired X-Ray scatter. The preferred material is a polycarbonate resin or acrylic material although other materials are believed to be similarly suitable for the intended use of the image quality phantom 30.

The image quality phantom 30 may be used during the initial calibration of the image system or at anytime thereafter to evaluate the performance of the image system. Typically, the image quality phantom 30 will be used whenever degradation of the image quality from the image system is suspected. The evaluation report will usually evaluate the sharpness, spatial linearity, brightness uniformity and signal or noise of the images either regionally, globally or both. The results of the evaluation will then be used to adjust the components of the image system or to provide image correction in the event of image distortion of the types known as pin cushion or barrel distortion.

FIG. 3 is illustrative of a prior art phantom for use in computer tomography and is disclosed more fully in U.S. Pat. No. 4,873,707.

A further improvement in the system of the present invention includes an arterial phantom 34 of the type shown in FIGS. 4–7.

The arterial phantom 34 of the present invention is preferably a generally elongate block shaped member with a telescopic shaped recess 36 therein as best shown in FIGS. 4–6. In the preferred form of the present embodiment, the arterial phantom has a lengthwise dimension of about 30 mm (FIG. 4) and a height of about 20 mm (FIG. 5). The arterial phantom 34 is preferably made of a polycarbonate or acrylic material which approximates the X-Ray scatter and distortion that occurs during an X-Ray of the coronary arteries of a patient. As illustrated in FIG. 6, the recess 36 of the arterial phantom preferably includes multiple decreasing diameter stepped cylindrical surfaces and is filled with an angiographic imaging dye such as RENOGRAPHIN. In the preferred embodiment, the recess 36 includes ten different diameter surfaces each having an identical length of about 5 mm. The diameter of the largest surface is preferably about 5 mm and the diameter of the smallest surface is preferably about 0.5 mm. FIG. 7 is a top view of the arterial phantom 36 of the present invention placed on the table of the imaging system.

As shown in FIG. 8, the procedure catheter 38 or a catheter of the same type, size and manufacturer of the catheter to be used during the procedure are placed on the table 12 of the imaging system to perform the image calibration step of the present invention. In this example, the table 12 may include adhesive type strips 37 to retain the procedure catheter 38 in the desired position relative to the arterial phantom. The data received from the in vitro imaging procedure catheter 38 and the arterial phantom 34 is used to create a regression curve which is developed from the arterial phantom plot over the range of diameters represented. Additionally, the imaged procedure catheter 38 and arterial phantom 34 are used to create a ratio of calipered-to-detected catheter diameters based on the known diameter of the catheter and the known diameter of the various portions of the arterial phantom 34. Thereafter, the tables of regression curves are stored and used in subsequent clinical applications of the analysis program. Finally, during the final pass of the analysis program over the data from the image of interest, the analysis program applies the regression correction data from the regression curve to modify the edge placement of the analysis program. As verification of this method, a pair of standard analysis program plots using the same arterial model before and after the application of the present invention are shown in FIGS. 9A and 9B. The plot of the diameter vs. the segment length of the arterial phantom 34 shown in FIG. 9A illustrates the nonlinear response of the analysis program and the over estimation of the measurements under 1 mm of a currently available analysis program without use of the devices and method of the present invention. The plot of the diameter vs. the segment length of the arterial phantom 34 shown in FIG. 9B illustrates the improvements to the linearity of diameter response and the significantly increased accuracy of measurements under 1 mm of the same currently available analysis program using the arterial phantom 34 and the method of the present invention.

What is claimed is:

1. A system for use in the quantitative measurement of a blood vessel or organ of interest of a patient, the system including:

an imaging phantom having a generally telescopically shaped recess formed therein and wherein said recess includes a plurality of known diameters and a radiographic dye therein;

a procedure catheter of known external diameter;

an imaging apparatus having a means for performing a dimensioned analysis on a blood vessel or organ of interest of a patient such that when said phantom and said procedure catheter are imaged by said imaging apparatus, an image apparatus specific diameter regression curve is created by said means for performing and said regression curve is applied to a subsequent image of the blood vessel or organ of interest of the patient to provide a correction factor to said subsequent image and increase the edge detection accuracy of said imaging apparatus.

2. The system of claim 1 further including said imaging phantom having a plurality of different known diameter and known length surfaces therein.

3. The system of claim 2 further including at least one of said known diameter and said known length surfaces having the same diameter as said length.

4. The system of claim 1 wherein said means for performing a dimensioned analysis further includes a means for creating an actual to imaged catheter diameter ratio which is applied by said means for performing a dimensioned analysis to said subsequent image which includes said procedure catheter and said blood vessel or organ of interest.

5. The system of claim 1 further including a second imaging phantom wherein said second imaging phantom includes a plurality of equidistantly spaced apart members therein and said spaced apart members are imaged by said image apparatus and data from said images is used to correct subsequently imaged images from said image apparatus to minimize distortion along the periphery of said subsequent images.

6. The system of claim 5 wherein said members of said second imaging phantom are ball shaped members having an X-Ray absorption characteristic similar to the X-Ray characteristics of said radiographic dye in said imaging phantom.

* * * * *